United States Patent [19]

Schramm

[11] Patent Number: 5,673,790

[45] Date of Patent: Oct. 7, 1997

[54] SHARPS DISPOSAL SERVICE

[76] Inventor: James J. Schramm, 1807 E. Grand Ave., Lindenhurst, Ill. 60046

[21] Appl. No.: 512,767

[22] Filed: Aug. 9, 1995

[51] Int. Cl.$^6$ .................................. A61L 2/16; A61M 5/32
[52] U.S. Cl. ......................... 206/366; 206/210; 604/110; 604/192
[58] Field of Search .......................... 206/365–367, 206/382, 210; 604/110, 192, 263

[56] References Cited

U.S. PATENT DOCUMENTS

| | | | |
|---|---|---|---|
| 2,400,722 | 5/1946 | Swan | 206/210 |
| 4,240,425 | 12/1980 | Akhavi . | |
| 4,474,734 | 10/1984 | Cooper . | |
| 4,728,321 | 3/1988 | Chen . | |
| 4,735,311 | 4/1988 | Lowe et al. . | |
| 4,917,243 | 4/1990 | Abrams et al. . | |
| 4,921,491 | 5/1990 | Champ . | |
| 4,936,449 | 6/1990 | Conard et al. . | |
| 4,950,242 | 8/1990 | Avarez | 604/110 |
| 4,982,842 | 1/1991 | Hollister . | |
| 5,037,400 | 8/1991 | Curry | 604/192 |
| 5,084,027 | 1/1992 | Bernard . | |
| 5,085,647 | 2/1992 | Henderson et al. . | |
| 5,184,721 | 2/1993 | Wengyn et al. | 206/366 |
| 5,207,653 | 5/1993 | Janjua et al. . | |
| 5,230,426 | 7/1993 | Keefe et al. | 206/366 X |
| 5,230,428 | 7/1993 | McShane . | |
| 5,303,822 | 4/1994 | Wengyn et al. | 206/366 |
| 5,304,148 | 4/1994 | Lannoye et al. . | |
| 5,347,078 | 9/1994 | Eckels | 206/365 X |
| 5,385,556 | 1/1995 | Wong et al. | 604/192 |
| 5,427,234 | 6/1995 | Upchurch | 206/210 |

*Primary Examiner*—Bryon P. Gehman
*Attorney, Agent, or Firm*—Marshall, O'Toole, Gerstein, Murray & Borun

[57] ABSTRACT

A sharps disposal device having a hollow housing and sharps-anchoring material for safe containment of contaminated medical sharps prior to permanent disposal. A flange stabilizes the disposal device on flat surfaces and provides a gripping surface for use in a one-handed technique for safe insertion of the contaminated medical sharps into the disposal device. Additionally, the disposal device may include a cover which positively secures the contaminated medical sharps after insertion into the disposal device.

12 Claims, 2 Drawing Sheets

SHARPS DISPOSAL SERVICE

FIELD OF THE INVENTION

This invention relates to the disposal of contaminated medical sharps, particularly I.V. needles and hypodermic needles. More particularly, the invention relates to an improved device for protecting users from needle sticks prior to the permanent disposal of contaminated medical sharps.

BACKGROUND OF THE INVENTION

An ongoing problem in the health care industry is a risk of exposure to serious diseases, such as HIV and hepatitis, through contact with contaminated medical instruments. Accidental needle punctures and contamination of open wounds by exposed portions of used sharp objects, such as scalpels, suture scissors, syringe needles, hollow needles used to withdraw blood, and needles used with I.V. lines (hereinafter generally "sharps"), present significant hazards to health care workers until such objects are safely discarded. The risk is reduced through the use of disposable instruments with protective sheaths and disposal vaults. However, the risk of contact still exists from the time the sharp instrument is used until it is deposited in a disposal vault.

Once a medical sharp is used, and thus contaminated, the user cannot merely lay the contaminated sharp to the side until a later time when disposal is more convenient. The user could forget the contaminated sharp, or the user or another person could accidentally come into contact with the sharp. The potential risk of undisposed contaminated sharps is even more acute where many people are working around a patient and someone could accidentally kneel or sit on the contaminated sharp. Such accidents are likely to occur to emergency room attendants or to paramedics at accident sites. Additionally, a person could receive a needle stick accidentally when the contaminated sharp is finally transported to the disposal vault. References to "needle sticks" are merely illustrative; other sharps pose similar hazards.

Health care professionals have attempted to reduce the risk of needle sticks by recapping the contaminated sharp in its original sheath after use. The sheath is typically a narrow tube with a locking mechanism similar to those described in U.S. Pat. Nos. 4,240,425, 4,474,734, 4,728,321, 4,735,311, and 5,085,647, which is primarily intended to protect the sharp prior to use. Normally, the opening in the sheath is small and recapping is accomplished by holding the sheath in one hand and inserting the used sharp through the opening until locked in the original position. Not only is the chance of sticking the hand holding the sheath during this procedure great, but the fact that the resheathing procedure requires two hands also poses a problem.

Generally, safety standards for disposal of contaminated sharps strongly recommend not recapping the devices with the original sheaths. OSHA regulations only permit recapping in certain situations, and in those situations the user must recap the sharp using either a mechanical device or a one-handed technique. Therefore, even a sheath such as the device disclosed in U.S. Pat. No. 5,304,148, which provides a shield to protect the hand holding the sheath, is not recommended for use. Although the shield protects the hand holding the sheath, a two-handed technique is still required to recap the sharp.

U.S. Pat. No. 4,917,243 discloses a device for disposing of a needle without recapping the needle in its original sheath. The device provides a container for the needle adapted to permit separation of the needle from a syringe without the user contacting the needle directly. Despite the separation feature, users must still use both hands: one hand to grasp the syringe, the other hand to grasp the container, as shown in FIG. 5a, 5b, and 5c of the patent. Therefore, use of this device still presents the risk of a two-handed technique.

Another solution to eliminate the risk of accidental needle sticks is to keep a sharps disposal vault near the patient for final disposal immediately after use. One such vault is disclosed in U.S. Pat. No. 4,936,449 which shows a container with a block of styrofoam and a lid. The device functions as a complete disposal system kept near the patient for final disposal of sharps immediately after use. While the vault appears to provide an ideal solution, the size of the device presents practical problems. First, vaults allow users to dispose of contaminated sharps from more than one patient or procedure before the device is full. The user could leave the vault around for several days before final disposal, increasing the risk of someone dropping, misplacing, or stealing the vault. Second, the vault can be too large either to transport or to place near the patient. This is especially problematic for paramedics who must carry their equipment to the patient's location in a tackle box or drug box and then work on the patient in a confined area.

OBJECTS OF THE INVENTION

It is an object of this invention to provide an improved disposal device for contaminated medical sharps that reduces the risk of needle sticks that can transmit serious diseases.

It is a further object of this invention that the user can insert contaminated medical sharps into the disposal device using a safe, one-handed technique.

It is yet another object of this invention to provide a disposal device that accepts multiple numbers and types of medical sharps used during a single patient procedure and retains the contaminated sharps if the device is bumped or dropped.

It is another object of this invention to provide containment for fluids draining from the contaminated sharp.

It is yet another object of this invention to provide a disposal device small enough for convenient transport to the patient site.

It is a further object of this invention to provide a safe vehicle for transporting the contaminated sharp from the patient site to a final disposal receptacle.

SUMMARY OF THE INVENTION

The present invention provides a sharps disposal device having a hollow tubular housing with an open, proximal end and a closed, distal end. A large slot, which allows easy insertion of at least one sharp, is located in the sidewall of the housing beginning at the proximal end and progressing toward the distal end. Located within the distal end of the housing is a penetrable, sharps-anchoring material, such as a low density polyolefin or polypropylene material, which frictionally grips the sharp and prevents it from dislodging from the housing. A flange extends from the proximal end of the housing and provides a gripping surface for a user's fingers while the sharp is pushed into the closed end by the user's thumb. The flange also elevates the proximal end to prevent drainage outside the device of fluids from the contaminated sharp. In a preferred embodiment, the flange has a flattened portion which prevents the disposal device from rolling and ensures that the slot is on top of the disposal device.

In a preferred form, the disposal device is large enough to hold several sharp objects. Because, for example, it is sometimes necessary for a medical care giver to employ more than one needle in administering an intravenous solution, the capability to hold multiple sharps is a desirable feature.

The disposal device is relatively simple in construction. The housing is preferably manufactured from a thermoplastic material which can be formed into the required shape by an injection molding process, although other materials and forming methods can be employed.

A preferred embodiment of the disposal device includes an arcuate cross-section. Thus, the portion of the housing adjacent the distal end has a circular cross-section, and the portion of the housing intersecting the slot has a semicircular cross-section. The cross-sectional geometry is not important as long as it allows easy access to the interior. Any cross-sectional shape is appropriate, including but not limited to rectangular, square, diamond, and square with rounded corners.

In another preferred embodiment, an absorbent material, such as cotton or any other absorbent material, is located in the housing between the housing distal end and the penetrable material. The absorbent material is an additional means for containment of fluids draining from the inserted sharps if the disposal device is inadvertently overturned from the flange base. The absorbent material could also be treated with a chemical to neutralize or kill viruses or bacteria contained in the bodily fluids on or in the sharp. A hollow reservoir containing a similar, sanitizing chemical could also be positioned in the distal end. The reservoir could be used with or without the absorbent material.

In another preferred embodiment, a means for covering the slot and the proximal end opening of the housing is provided to positively secure the contaminated sharp or sharps in the housing. One optional embodiment of the covering means is a cover manufactured from the same material as the housing and attached to the housing by an integral hinge. In this embodiment, when the cover is rotated about the integral hinge to the closed position, the cover can be locked into place using industry standard means for snap locking pieces together.

Another optional embodiment for the covering means is a detached cover that slides into a position covering the slot and the proximal end opening. As with the attached cover, the detached cover can be locked into a closed position using a standard snap locking means. Yet another optional embodiment uses an adhesive backed flexible label which can be used to cover the open portion of the sharps disposal device after a contaminated sharp is inserted. This label could be either an attached cover or a separate, detached cover. Printed indicia on the label could provide additional instructions for the user, i.e., a warning or disposal instructions. In addition to the options presented, other covering means will be apparent to those skilled in the art.

The invention may best be understood by reference to the following description when considered with the accompanying illustrations.

DETAILED DESCRIPTION OF THE DRAWINGS

Figure 4:
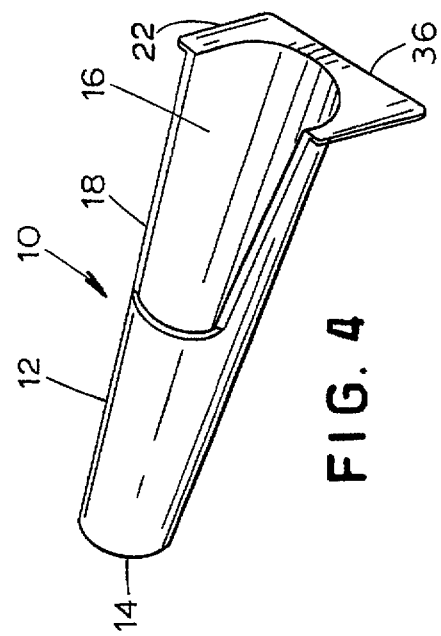
FIG. 4 is an isometric view of the sharps disposal device.

Referring to FIGS. 1–4, a sharps disposal device used for the safe disposal of contaminated medical sharps is indicated generally by the numeral 10. The disposal device 10 is an elongated, hollow housing 12, manufactured from a thermoplastic material by any desired conventional molding procedure, having a closed, distal end portion 14 and an open, proximal end portion 16. A slot 18 in the sidewall of the housing 12 is located adjacent the proximal end portion 16 and extends toward the distal end portion 14. The slot 18 is wide enough to facilitate insertion of contaminated sharps of varying sizes into the housing 12.

A penetrable, sharps-anchoring material 20, such as a low density polyolefin foam, is mounted in the distal end portion 14 of the housing 12. If desired, an adhesive or mechanical means (not shown) may be used to affix the sharps-anchoring material 20 to the sidewall of the housing 12. A flange 22 extends from the proximal end portion 16 of device 10 to provide a gripping surface 24 during the insertion of a contaminated sharp 30. The downward protrusion of the flange 22 elevates the proximal end portion 16 higher than the distal end portion 14 to ensure containment of any fluids draining from the contaminated sharp 30.

Figure 3:
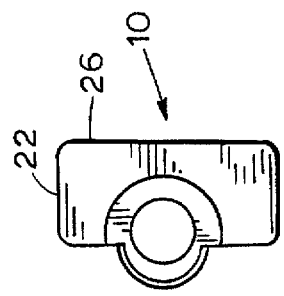
FIG. 3 is a side elevational view of the sharps disposal device.
Figure 2:
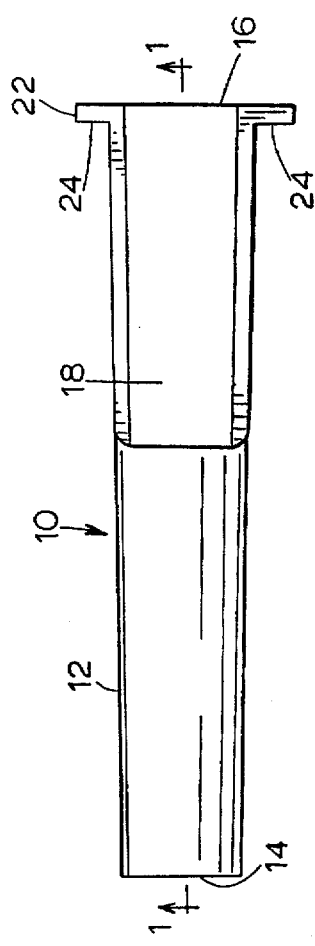
FIG. 2 is a top view of the sharps disposal device.

FIG. 3 illustrates a preferred embodiment of the disposal device 10 where the flange 22 has a flattened edge portion 26. The flattened edge portion 26 ensures that the slot 18 is on top of the housing 12 and prevents the disposal device 10 from rolling. FIG. 3 also illustrates that the housing 12 of this embodiment of the disposal device 10 generally has an arcuate cross-section, with the portion proximate the distal end portion 14 having a circular cross-section and the portion intersecting the slot 18 having a semicircular cross-section.

Figure 1:
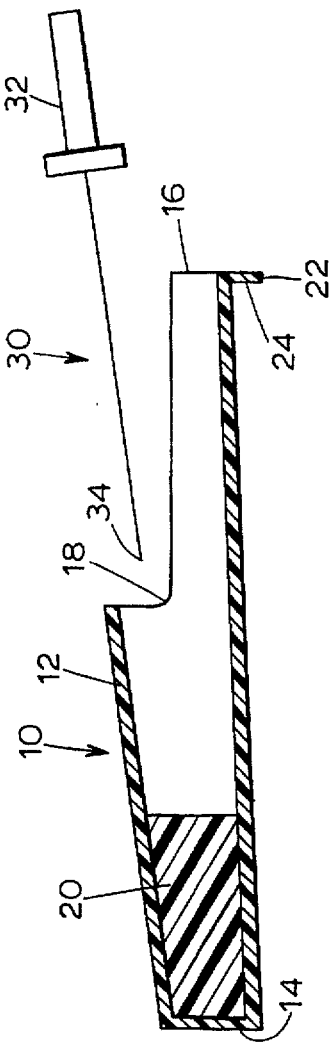
FIG. 1 is a sectional elevational view of the sharps disposal device with a contaminated sharp entering downwardly and inwardly through the slot and proximal end opening.

Referring to FIG. 1, the one-handed technique for inserting a contaminated sharp 30 into the disposal device 10 will be described. The disposal device 10 is placed on a flat surface with the slot 18 facing up and the proximal end portion 16 and flange 22 toward the user. While the user holds the contaminated sharp 30 by the hub 32 in one hand, the user advances the contaminated sharp 30 downwardly and inwardly into the housing 12 through the slot 18 and proximal end portion 16 until the point 34 of the contaminated sharp 30 touches the sharps-anchoring material 20. The user places the index and middle fingers of the same hand on the gripping surface 24 of the flange 22 on either side of the slot 18 and housing 12. Simultaneously, the thumb applies pressure to the contaminated sharp 30, pushing the contaminated sharp 30 into the sharps-anchoring material 20 until the contaminated sharp 30 will go no farther. At this point, the contaminated sharp 30 is safely contained and ready for final disposal.

Figure 5:
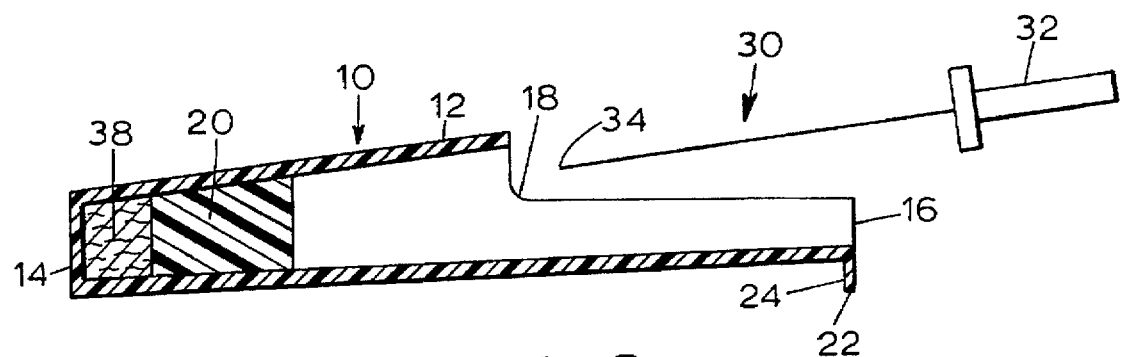
FIG. 5 is a sectional elevational view of a sharps disposal device including an absorbent material at the closed, distal end of the device.

FIG. 5 illustrates the sharps disposal device 10 shown in FIG. 1 with the addition of an absorbent material 38 located in the housing 12 between the distal end portion 14 and the sharps-anchoring material 20. During the one-handed technique described above, the point 34 of the contaminated sharp 30 is pushed through the sharps-anchoring material 20 and into the absorbent material 38. The absorbent material 38 provides a capillary network for containment of fluid draining from the point 34 of the contaminated sharp 30. In other embodiments, the absorbent material 38 is either treated with a contaminant neutralizing chemical, or replaced or integrated with a hollow reservoir filled with the contaminant neutralizing chemical (not shown).

Figure 6A:
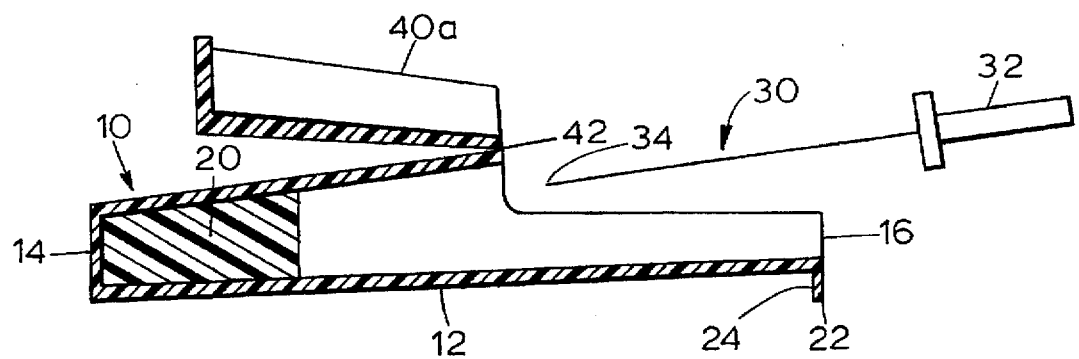
FIG. 6a is a sectional elevational view of a sharps disposal device including a covering means attached to the housing by an integral hinge.
Figure 6B:
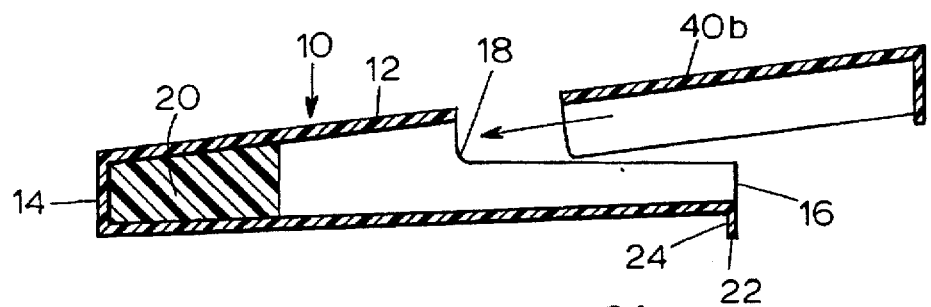
FIG. 6b is a sectional elevational view of another embodiment of the sharps disposal device including a detached covering means.
Figure 6C:
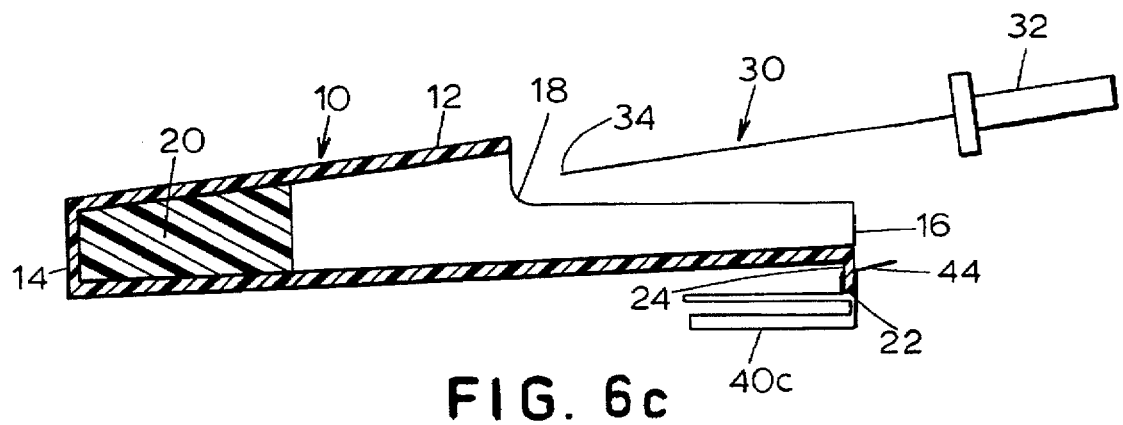
FIG. 6c is a sectional elevational view of a third embodiment of the sharps disposal device including an adhesive backed covering means.

FIGS. 6a, 6b, and 6c illustrate the disposal device 10 shown in FIG. 1 with the addition of various means for covering slot 18 and proximal end portion 16. Each covering means provides increased positive retention of the contaminated sharp 30 after insertion into the device 10. An attached cover 40a is illustrated in FIG. 6a in the open position. The attached cover 40a is affixed to the housing 12 by an integral hinge 42. The attached cover 40a is rotated about the integral hinge 42 to the closed position where the attached cover 40a locks into place by standard means for snap locking connecting pieces (not shown).

FIG. 6b illustrates an embodiment where the covering means is a detachable cover 40b. The detached cover 40b is slid onto the housing 12 and locks into place by any industry standard means for snap locking connecting pieces (not shown).

FIG. 6c shows a third embodiment of the covering means wherein a label 40c coated with an adhesive material is attached to the flange 22. This label could also be provided loose and applied after peeling off a backing. After inserting the contaminated sharp 30 into the sharps disposal device 10, the label 40c is grasped by a tab 44 and pulled over the proximal end portion 16 and the slot 18. The adhesive material on the label 40c adheres to the flange 22 and housing 18 to retain the contaminated sharp 30. Printed indicia on the front surface of label 40c could also function as a warning label and provide final disposal instructions.

Various modifications, alternative constructions and equivalents may be employed without departing from the scope of the invention as exemplified in the foregoing description and further defined in the following claims.

What is claimed:

1. Apparatus for storing a plurality of contaminated sharps, said apparatus comprising:

an elongated, hollow housing having a closed, distal end portion, an open, proximal end portion, and having an interior volume sufficient to hold more than one sharp;

a large slot in said housing, adjacent said open proximal end portion and extending a substantial length along said housing from said proximal end portion, said large slot having a width extending substantially the width of said housing and sufficient to permit the insertion of sharps of varying types downwardly and inwardly into said apparatus, through said large slot;

a penetrable, sharps-anchoring material mounted in said hollow housing, adjacent said closed, distal end portion; and a flanged gripping surface at said open, proximal end portion for assisting in the insertion of contaminated sharps into said apparatus.

2. Apparatus according to claim 1 wherein a cross-sectional area of said proximal end portion is greater than a cross-sectional area of said distal end portion.

3. Apparatus according to claim 1 wherein said flanged gripping surface has a flattened edge portion for preventing said apparatus from rolling.

4. Apparatus according to claim 1 wherein said hollow housing has an arcuate cross-section.

5. Apparatus according to claim 4 wherein said cross-section is circular.

6. Apparatus according to claim 1 further comprising a penetrable, absorbent material in said hollow housing, between said closed, distal end portion and said penetrable, sharps-anchoring material.

7. Apparatus according to claim 6 wherein said absorbent material is treated with a contaminant neutralizing chemical.

8. Apparatus according to claim 1 further comprising a hollow reservoir in said hollow housing, between said closed, distal end portion and said penetrable, sharps-anchoring material, said hollow reservoir being filled with a contaminant neutralizing chemical.

9. Apparatus according to claim 1 further comprising a means for covering said slot and said open, proximal end portion.

10. Apparatus according to claim 9 wherein said covering means comprises a snap lock cover attached to said housing by an integral hinge at said slot adjacent said closed, distal end portion and detachably attached at said open, proximal end portion.

11. Apparatus according to claim 9 wherein said covering means comprises a detachable snap lock cover which slides onto said housing and detachably attaches about said slot and said open, proximal end portion.

12. Apparatus according to claim 9 wherein said covering means comprises a label having a rear surface coated with an adhesive material, said label attached to said flange, and said label extending over said slot and open, proximal end portion, after insertion of said contaminated sharps, with said adhesive material adhering to said housing and said flange.

* * * * *